(12) United States Patent
Witham et al.

(10) Patent No.: US 8,859,623 B1
(45) Date of Patent: Oct. 14, 2014

(54) METHODS AND COMPOSITIONS OF STABLE PHENYLEPHRINE FORMULATIONS

(71) Applicant: Paragon BioTeck, Inc., Portland, OR (US)

(72) Inventors: Patrick H. Witham, Eugene, OR (US); Sailaja Machiraju, Beaverton, OR (US); Lauren Mackensie-Clark Bluett, Milwaukie, OR (US)

(73) Assignee: Paragon Bioteck, Inc., Portland, OR (US)

( * ) Notice: Subject to any disclaimer, the term of this patent is extended or adjusted under 35 U.S.C. 154(b) by 0 days.

(21) Appl. No.: 14/080,771

(22) Filed: Nov. 14, 2013

(51) Int. Cl.
*A61K 31/137* (2006.01)

(52) U.S. Cl.
CPC .................................. *A61K 31/137* (2013.01)
USPC ........................................................ 514/653

(58) Field of Classification Search
None
See application file for complete search history.

(56) References Cited

U.S. PATENT DOCUMENTS 4,260,600 A * 4/1981 Valle .............................. 424/720

OTHER PUBLICATIONS

Akorn, Inc., package insert for phenylephrine hydrochloride solution/drops, at http://dailymed.nlm.nih.gov/dailymed/lookup.cfm?setid=c5c51d8b-b50b-4c77-9d55-f64c14b0d0e5, revised Sep. 2011.*

Brown, et al., "Activities of octopamine and synephrine stereoisomers on α-adrenoceptors." Br. J. Pharmacol. (1988), 93, 417-429.

El-Shibini, et al. "The Stability of Phenylephrine—Part 1: The Rate of Degradation of the Amino Group." Arzneimittelforschung. Apr. 1969;19(4):676-8.

El-Shibini, et al. "The Stability of Phenylephrine—Part 2: The discolouration reaction and the influence of some ions on the rate of degradation of the drug." Arzneimittelforschung. May 1969;19(5):828-31.

El-Shibini, et al. "The Stability of Phenylephrine—Part 3: The racemisation reaction." Arzneimittelforschung. Sep. 1969;19(9):1613-4.

Millard, et al., "The Stability of Aqueous Solutions of Phenylephrine at Elevated Temperatures: Identification of the Decomposition Products." J. Pharm. Pharmac., 1973, 25. Suppl., 24P-31P.

"Report of the International Workshop on in Vitro Methods for Assessing Acut Systemic Toxicity." Results of an International Workshop Organized by the Interagency Coordinating Committee on the Validation of Alternative Methods (ICCVAM) and the National Toxicology Program (NTP) Interagency Center for the Evaluation of Alternative Toxicological Methods (NICEATM); pp. 1-370.

Zaczek, et. al., "The effect of phenylephrine on pain and flare intensity in eyes with uveitis." Acta Ophthalmol Scand. Oct. 2000;78(5):516-8.

* cited by examiner

*Primary Examiner* — David J Blanchard
*Assistant Examiner* — Barbara Frazier
(74) *Attorney, Agent, or Firm* — Wilson Sonsini; Goodrich & Rosati

(57) ABSTRACT

The invention is directed to methods and compositions of stabilizing phenylephrine formations. The composition has good time-dependent stability at low temperature and has no change in its outward appearance even after having been stored at least 6 months.

13 Claims, 4 Drawing Sheets

METHODS AND COMPOSITIONS OF STABLE PHENYLEPHRINE FORMULATIONS

BACKGROUND OF THE INVENTION

Phenylephrine is a selective α1-adrenergic receptor agonist used primarily as a decongestant, as an agent to dilate the pupil, and to increase blood pressure. Phenylephrine is marketed as a substitute for the decongestant pseudoephedrine, though clinical studies differ regarding phenylephrine's effectiveness in this role.

SUMMARY OF THE INVENTION

In accordance with the present invention, the present invention provide a composition comprising at least 95% R-phenylephrine hydrochloride and an aqueous buffer, wherein the composition substantially maintains an initial chiral purity of R-phenylephrine hydrochloride for at least 6 months stored between −10 to 10 degree Celsius.

In another aspect, provided herein are methods of stabilizing a phenylephrine hydrochloride composition comprising storing a solution of aqueous R-phenylephrine hydrochloride at less than 10 degree Celsius, wherein the composition substantially maintains the initial chiral purity of R-phenylephrine hydrochloride for at least 6 months.

In one aspect, provided herein are methods of assaying chiral purity of R-phenylephrine hydrochloride, wherein the chiral purity is determined by chiral column chromatography, optical rotation, capillary electrophoresis, circular dichroism, or Nuclear Magnetic Resonance.

In another aspect provides compositions comprising R-phenylephrine hydrochloride, wherein the composition substantially maintains the initial chiral purity of R-phenylephrine hydrochloride for at least 6 months.

In another aspect provides methods of dilating the pupil comprising administering a composition comprising R-phenylephrine hydrochloride topically to a mammal, wherein the composition substantially maintains the initial chiral purity of R-phenylephrine hydrochloride for at least 6 months.

In another aspect provides methods of treating Uveitis in a subject comprising administering a composition comprising R-phenylephrine hydrochloride to said subject, wherein the composition substantially maintains the initial chiral purity of R-phenylephrine hydrochloride for at least 6 months In another aspect provides methods of performing certain ocular testing such as ultrasonography, provocative closed angle glaucoma test, Retinoscopy, compromised circulation (i.e., blanching test), Refraction, fundus examination comprising administering a composition comprising R-phenylephrine hydrochloride, wherein the composition substantially maintains the initial chiral purity of R-phenylephrine hydrochloride for at least 6 months.

In another aspect provides methods of aiding surgical procedures requiring visualization of the posterior chamber comprising administering a composition comprising R-phenylephrine hydrochloride to a subject, wherein the composition substantially maintains the initial chiral purity of R-phenylephrine hydrochloride for at least 6 months.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
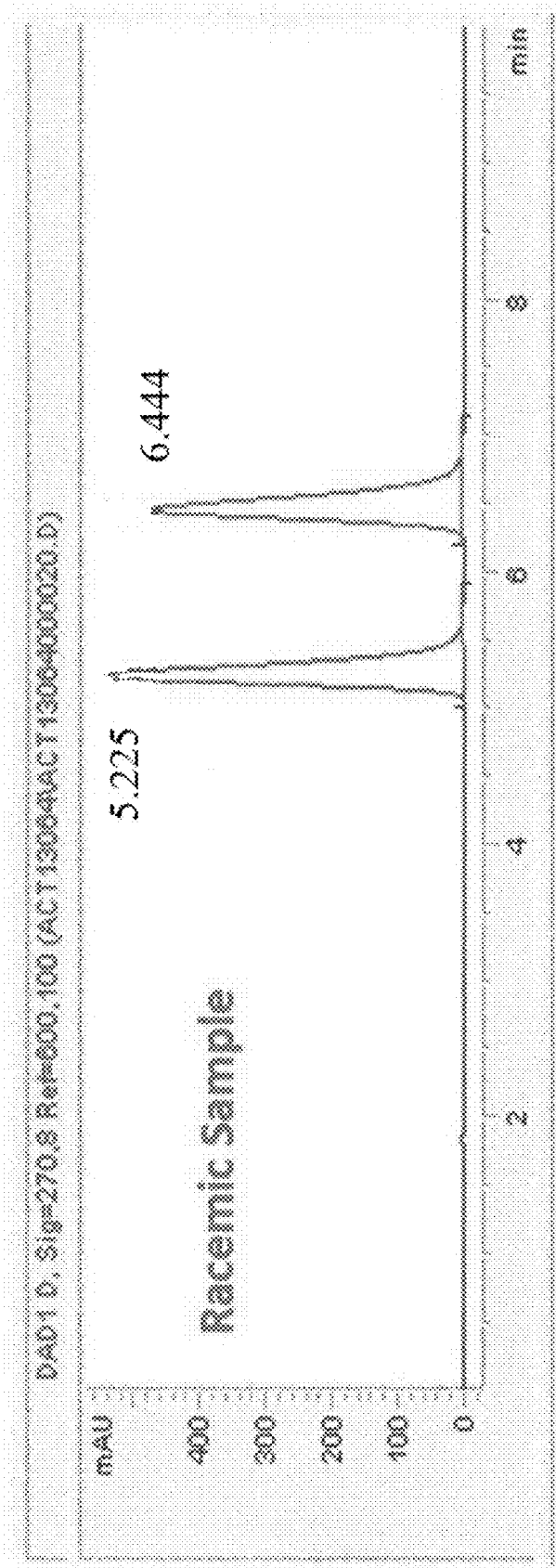
FIG. 1 shows a HPLC chromatogram of racemic R-phenylephrine hydrochloride by a chiral column purification (OJ-RH (150×4.6) mm). Two peaks at the retention time 5.225 minutes and 6.444 minutes are shown.

Phenylephrine differs chemically from epinephrine only in lacking one hydroxyl group (OH) in the four position on the benzene ring. It is a bitter-tasting crystalline material soluble in water and alcohols, with a melting point of 140°-145° C. Chemically it is Benzenemethanol, 3-hydroxy-α-[(methylamino)methyl]-, hydrochloride or (R)-(−)-m-hydroxy-α-[methylamino)methyl]benzyl alcohol hydrochloride with the following chemical structure.

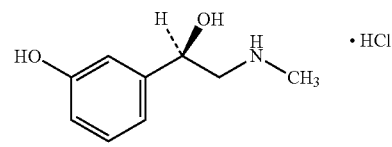

It is known in the art that a Phenylephrine Hydrochloride solution should be stored protected from light. The benzylic hydrogen is acidic and can be deprotonated easily. The hydroxyl group may be oxidized to form a carbonyl moiety conjugated with phenyl group, especially with help of the adjacent basic amino group. Thus, it is known in the art that a Phenylephrine Hydrochloride solution should be stored protected from light. For example, an insert from a commercially available Phenylephrine Hydrochloride Ophthalmic Solution provides that the solution should be stored at 20° to 25° C. (USP controlled room temperature) and keep container tightly closed. Do not use if solution is brown or contains precipitate. (AKORN Package Insert)

However, a solution under such condition often turns brown over time despite of carefully keeping container tightly closed at 20° to 25° C. (USP controlled room temperature). Those packages containing the brown solution cannot be used and thus create waste.

The present invention provides the improvement to overcome such instability problem.

In some embodiments, there are provided a composition comprising at least 95% R-phenylephrine hydrochloride and an aqueous buffer for substantially maintaining chiral purity of R-phenylephrine hydrochloride for at least 6 months, the improvement comprising storing the composition between −10 to 10 degree Celsius. In certain embodiments, the composition is stored between 2 to 8 degree Celsius. In certain embodiments, the composition comprises at least 99% or 99.3%, R-phenylephrine hydrochloride. In certain embodiments, the chiral purity of R-phenylephrine hydrochloride is at least 95%, 97%, 99%, or 99.5% of the initial chiral purity after 6 months. In certain embodiments, the composition comprises 2.5% w/v or 10% w/v R-phenylephrine hydrochloride by weight. In certain embodiments, the composition further comprises a preservative such as benzalkonium chloride, stearalkonium chloride, polyaminopropyl biguanide, or the like. In some embodiments, the composition is in a 1-15 ml plastic or glass bottle. In some embodiments, the composition is in a glass or plastic bottle of about 2 ml, about 3 ml, about 5 ml, about 10 ml or about 15 ml. In certain embodiments, the plastic or glass bottle is opaque.

In some embodiments provide methods of stabilizing a phenylephrine hydrochloride composition such as a solution of aqueous R-phenylephrine hydrochloride at less than 10 degree Celsius wherein the composition substantially maintains the initial chiral purity of R-phenylephrine hydrochloride for at least 6 months.

In some embodiments provide herein compositions comprising R-phenylephrine hydrochloride, wherein the composition substantially maintains the initial chiral purity of R-phenylephrine hydrochloride for at least 6 months.

In some embodiments, the composition is stored at −10 to 10 degree Celsius. In certain embodiments, the composition is stored at −5 to 10 degree Celsius. In certain embodiments, the composition is stored at 0 to 10 degree Celsius. In certain embodiments, the composition is stored at 2 to 8 degree Celsius.

The term "substantial" or "substantially maintains" described herein refers to not more than 15% deviation of the initial purity. In some embodiments, the chiral purity of the composition is at least 85%, 90%, 95%, 97%, 99%, 99.1%, 99.2%, 99.3%, 99.4%, 99.5%, 99.6%, 99.7%, 99.8% or 99.9% of the initial chiral purity.

In some embodiments provide herein methods of assaying chiral purity of R-phenylephrine hydrochloride, wherein the chiral purity is determined by chiral column chromatography, optical rotation, capillary electrophoresis, circular dichroism, or Nuclear Magnetic Resonance.

In certain embodiments, the chiral purity is determined by chiral column chromatography.

Chiral Column Chromatography

Chiral column chromatography is a variant of column chromatography in which the stationary phase contains a single enantiomer of a chiral compound rather than being achiral. The two enantiomers of the same analyte compound differ in affinity to the single-enantiomer stationary phase and therefore they exit the column at different times.

The chiral stationary phase can be prepared by attaching a suitable chiral compound to the surface of an achiral support such as silica gel, which creates a Chiral Stationary Phase (CSP). Many common chiral stationary phases are based on oligosaccharides such as cellulose or cyclodextrin (in particular with β-cyclodextrin, a seven sugar ring molecule). As with all chromatographic methods, various stationary phases are particularly suited to specific types of analytes.

The packing material of the chiral column may be amylose tris(3,5-dimethylphenylcarbamate), β-cyclodextrin, cellobiohydrolase, selector R-(−)-N-(3,5-dinitrobenzoyl)-phenylglycine, cellulose tris(3,5-dimethylphenylcarbamate), cellulose tris(3,5-dichlorophenylcarbamate), or combinations thereof. In some embodiments, the chiral column for analytical purpose is packed with amylose tris(3,5-dichlorophenylcarbamate). The column may have a packing particle of a size of about 3 μm to about 50 μm. In some embodiments, the column has a packing particle a size of about 3 μm, 5 μm, 10 μm, 20 μm, 30 μm, 40 μm, or 50 μm. In certain embodiments, the column has a packing particle a size of about 3 μm.

In some embodiments, when using a chiral column system, the first mobile phase is non-polar solvent such as n-hexane, n-pentane, and the like, and the second mobile phase is polar solvent such as isopropanol, ethanol, methanol, or the like. In certainly embodiments, the mobile phase comprises small amount of amine such as ethylenediamine. The first mobile phase may be present in an amount of about 75% to about 95% by volume and the second mobile phase is present in an amount of about 5% to about 25% by volume. In some embodiments, the first mobile phase is present in an amount of about 85% by volume and the second mobile phase is present in an amount of about 15% by volume with or without ethylenediamine.

Other Chiral Compound Analysis Methods

There are several chiral compound purification and analysis methods available besides chiral column chromatography. For example, it is known in the art chiral purity can be determined by optical rotation. In some embodiments, the chiral purity of R-phenylephrine hydrochloride in the stabilized compositions and methods thereof can be determined by comparison of optical rotation of pure R-phenylephrine hydrochloride.

Optical Purity Measured by Optical Rotation

Molecules with chrial centers cause the rotation of plane polarised light and are said to be "optically active" (hence the term optical isomers). Enantiomeric molecules rotate the plane in opposite directions but with the same magnitude. This provides a means of measuring the "optical purity" or "enantiomeric excess (ee)" of a sample of a mixture of enantiomers.

Specific rotation is a physical property like boiling point and can be looked up in references. It is defined according to the following equation based on the experimental measurements: Specific rotation $[\alpha]D = \alpha_{obs}/cl$ where "$\alpha_{obs}$" is the experimentally observed rotation, "c" is the concentration in g/ml and "l" is the path length of the cell used expressed in dm (10 cm).

A non-racemic mixture of two enantiomers will have a net optical rotation. It is possible to determine the specific rotation of the mixture and, with knowledge of the specific rotation of the pure enantiomer, the optical purity can be determined.

% Optical purity of sample=100*(specific rotation of sample)/(specific rotation of a pure enantiomer)

In some embodiments, there are provided methods of assaying chiral purity of R-phenylephrine hydrochloride, wherein the chiral purity is determined by optical rotation. In certain embodiments, the optical rotation is determined by comparison of optical rotation of pure R-phenylephrine hydrochloride.

Capillary Electrophoresis

Capillary electrophoresis (CE), also known as capillary zone electrophoresis (CZE), can be used to separate ionic species by their charge and frictional forces and hydrodynamic radius.

Capillary electrophoresis (CE) in general offers highly efficient separations. To achieve chiral separation, the capillary is filled with a separation buffer containing a chiral additive. Although many chiral selectors have been used successfully, the most comprehensive separation strategies have been achieved with highly sulfated cyclodextrins. In some embodiments, the chiral purity of the compositions provided herein is determined by capillary electrophoresis. In certain embodiments, the capillary electrophoresis uses cyclodextrin or its derivatives (such as sulfated cyclodextrins).

Chiral Purity Measured by Circular Dichroism

Circular dichroism (CD) refers to the differential absorption of left and right circularly polarized light. This phenomenon is exhibited in the absorption bands of optically active chiral molecules. CD spectroscopy has a wide range of applications in many different fields. For example, vibrational circular dichroism, which uses light from the infrared energy region, is used for structural studies of small organic molecules, and most recently proteins and DNA. In general, this phenomenon will be exhibited in absorption bands of any optically active molecule. As a consequence, circular dichroism is exhibited by biological molecules, because of their dextrorotary and levorotary components. Even more important is that a secondary structure will also impart a distinct CD to its respective molecules.

Optical rotation and circular dichroism stem from the same quantum mechanical phenomena and one can be derived mathematically from the other if all spectral information is provided. In some embodiments, the chiral purity is determined by circular dichroism. In certain embodiments, the chiral purity is determined by Fourier transform infrared vibrational circular dichroism (FTIR-VCD). A skilled person in the art can readily apply the general knowledge and procedure to determine chirality of the compositions provided herein.

NMR Spectroscopy of Stereoisomers

It is known in the art that NMR spectroscopy techniques can determine the absolute configuration of stereoisomers such as cis or trans alkenes, R or S enantiomers, and R,R or R,S diastereomers. In a mixture of enantiomers, these methods can help quantify the optical purity by integrating the area under the NMR peak corresponding to each stereoisomer. Accuracy of integration can be improved by inserting a chiral derivatizing agent with a nucleus other than hydrogen or carbon, then reading the heteronuclear NMR spectrum: for example fluorine-19 NMR or phosphorus-31 NMR. Mosher's acid contains a —CF3 group, so if the adduct has no other fluorine atoms, the 19F NMR of a racemic mixture shows just two peaks, one for each stereoisomer. In some embodiments, the chiral purity of the compositions provided herein is determined by Nuclear Magnetic Resonance Spectroscopy (NMR). In certain embodiments, a chirally pure complexing reagent (i.e., a chiral derivatizing agent) is used in measuring NMR. A skilled person in the art can readily utilize NMR and any suitable chiral complexing agent to determine the chirality of the compositions provided herein.

Dosage Forms and Strengths

In some embodiments, the stabilized compositions provided herein comprise a solution of 2.5% w/v or 10% w/v R-phenylephrine hydrochloride by weight. In certain embodiments, the compositions further comprise sodium phosphate monobasic, sodium phosphate dibasic, boric acid and benzalkonium chloride. The followings are non-limited exemplary compositions:

Phenylephrine Hydrochloride Ophthalmic Solution, 2.5% is a clear, colorless to yellowish, sterile topical ophthalmic solution containing phenylephrine hydrochloride 2.5%.

Phenylephrine Hydrochloride Ophthalmic Solution, 10% is a clear, colorless to yellowish, sterile topical ophthalmic solution containing phenylephrine hydrochloride 10%.

Application of the Stabilized Compositions Comprising R-Phenylephrine Hydrochloride It has been established that Phenylephrine Hydrochloride Ophthalmic Solution is recommended as a vasoconstrictor, decongestant, and mydriatic in a variety of ophthalmic conditions and procedures. Some of its uses are for pupillary dilation in uveitis (to prevent or aid in the disruption of posterior synechia formation), for many ophthalmic surgical procedures and for refraction without cycloplegia. Phenylephrine Hydrochloride Ophthalmic Solution may also be used for funduscopy and other diagnostic procedures.

For example, R-Phenylephrine is used to dilate the iris through α-adrenergic stimulation of the iris dilator muscle. Sympathetic stimulation of the ciliary muscle is believed to be inhibitory, decreasing accommodative amplitude. R-Phenylephrine is formulated in an eye drop to dilate the pupil in order to facilitate visualization of the retina. It is often used in combination with tropicamide as a synergist when tropicamide alone is not sufficient. Surprisingly it was found that S-Phenylephrine dilated the eye only slightly more than that was untreated. Thus it is important that an eye drop containing Phenylephrine Hydrochloride used for dilation of the pupil contains predominantly the R-isomer in order to maintain maximum efficacy of the ophthalmic solution.

Sympathetic innervation leads to pupillary dilation. It is innervated by the sympathetic system, which acts by releasing noradrenaline, which acts on α1-receptors causing dilation.

The alpha-1 ($α_1$) adrenergic receptor is a G protein-coupled receptor (GPCR) associated with the $G_q$ heterotrimeric G-protein. It consists of three highly homologous subtypes, including $α_{1A}$-, $α_{1B}$-, and $α_{1D}$-adrenergic. Catecholamines like norepinephrine (noradrenaline) and epinephrine (adrenaline) signal through the $α_1$-adrenergic receptor in the central and peripheral nervous systems.

Phenylephrine is a selective $α_1$-adrenergic receptor agonist used primarily as a decongestant, as an agent to dilate the pupil, and to increase blood pressure. Dilation is controlled by the dilator pupillae, a group of muscles in the peripheral ⅔ of the iris. Sympathetic innervation begins at the cortex with the first synapse at the cilliospinal center (also known as Budge's center after German physiologist Julius Ludwig Budge). Post synaptic neurons travel down all the way through the brain stem and finally exit through the cervical sympathetic chain and the superior cervical ganglion. They synapse at the superior cervical ganglion where third-order neurons travel through the carotid plexus and enter into the orbit through the first division of the trigeminal nerve.

In the anesthetized rats, infusion of large amount of (+)-epinephrine, (+)-norepinephrine, epinine, and (−)- or (+)-phenylephrine induces tachyphylaxis to vasopressor effect of (−)-epinephrine, (−)-norepinephrine, and tetraethylammonium. The tachyphylactic potency of the amines was (−)-phenylephrine (R-phenylephrine)>epinine>(+)-norepinephrine=(+)-epinephrine>(+)-phenylephrine.

Two ophthalmic formulations, formulated 10% Phenylephrine hydrochloride (S-isomer) and the exemplary invention composition, 10% Phenylephrine hydrochloride (R-isomer)

were tested for their ocular activity in NZW rabbits. It was observed that formulated S-isomer showed minimal dilation, responded to light exposure and constricted slightly more slowly than the untreated eye, where as the exemplary invention composition, 10% Phenylephrine hydrochloride showed maximal dilation with in 15 min of dosing and the pupil did not respond to light and remained dilated for 4 hrs.

According to the above study it could be postulated that, when an ophthalmic solution of phenylephrine hydrochloride, (R-isomer) containing S-isomer as an impurity is used for dilation of pupil, the s-isomer may cause the saturation of the a-adrenergic receptors resulting in the decrease in the response of the drug after its administration (tachyphylasis). Furthermore, the presence of S-isomer in the ophthalmic solution may lead to poor/delayed dilation of the pupil.

In some embodiments provide methods of dilating the pupil comprising administering a composition comprising R-phenylephrine hydrochloride topically to a mammal, wherein the composition substantially maintains the initial chiral purity of R-phenylephrine hydrochloride for at least 6 months. It is evident from the literature that the pharmacological evaluation of both R & S-Phenylephrine hydrochloride is not same. R-Phenylephrine is referenced as useful synthetic adrenergic drug.

Uveitis

Uveitis is, broadly, inflammation of the uvea. The uvea consists of the middle, pigmented, vascular structures of the eye and includes the iris, ciliary body, and choroid. Uveitis requires an urgent referral and thorough examination by an ophthalmologist or Optometrist and urgent treatment to control the inflammation. Anterior uveitis (iritis) affects the front portion of the eye, intermediate uveitis (cyclitis) affects the ciliary body, and posterior uveitis (choroiditis) affects the back portion of the uvea. Diffuse uveitis affects all portions of the uvea. Anterior uveitis commonly occurs in conjunction with juvenile rheumatoid arthritis, but does not manifest in all juvenile arthritis patients. Uveitis is most likely to be present in juvenile arthritis patients with pauciarticular disease (fewer than five joints involved), a positive anti-nuclear antibody test, and a negative rheumatoid factor test. It has been demonstrated that after phenylephrine hydrochloride ophthalmic solution instillation, flare intensity and pain were significantly decreased only in eyes with iridocyclitis and without fibrinoid reaction (FR). The decreasing level of flare intensity, and paralysis of the pupil after phenylephrine instillation seem to alleviate pain in those eyes. See e.g., Zaczek, et. al., Acta Ophthalmol Scand. 2000 October; 78(5):516-8.

In some embodiments provide methods of treating Uveitis in a subject comprising administering a composition comprising R-phenylephrine hydrochloride to said subject, wherein the composition substantially maintains the initial chiral purity of R-phenylephrine hydrochloride for at least 6 months.

In some embodiments provide methods of performing certain ocular testing such as ultrasonography, provocative closed angle glaucoma test, Retinoscopy, compromised circulation (i.e., blanching test), Refraction, fundus examination comprising administering a composition comprising R-phenylephrine hydrochloride, wherein the composition substantially maintains the initial chiral purity of R-phenylephrine hydrochloride for at least 6 months.

In some embodiments provide methods of aiding surgical procedures requiring visualization of the posterior chamber comprising administering a composition comprising R-phenylephrine hydrochloride, wherein the composition substantially maintains the initial chiral purity of R-phenylephrine hydrochloride for at least 6 months.

After presentation of R-phenylephrine hydrochloride ophthalmic solution 2.5% or 10% to the ocular surface, a broad variation in the delay of onset of dilation is widely reported, varying between 20-to-30 minutes and as much as up to 60 minutes. While a number of contributors to this delay of onset have been theorized, the absence of phenylephrine hydrochloride's pharmacologic activity in the eye due to the presence of S-phenylephrine may in fact be the explanation for such delay.

Dropper Bottle or Storage Bottle

Conventional dropper bottles for administering ophthalmic fluid are well known in the prior art. The basic commercial design of such dropper bottles has remained fairly unchanged over the last several decades: a squeezable container is provided with a tapered dispenser that terminates in a discharge aperture. To administer ophthalmic fluid, the discharge aperture is aligned above a target eye and the bottle is squeezed to urge out a drop or dose of the fluid.

Alternatively, liquid dispensers have been developed in which the formulation is supplied from a storage bottle through a dropper, for example (dropper bottles or EDO-Ophthiols). The aqueous formulation usually flows out of the dropper opening as a result of manual pressure being applied to the compressible storage bottle.

In some embodiments, the composition described herein is stored in a plastic or glass bottle. In certain embodiments, the plastic bottle is a low-density polyethylene bottle. In certain embodiments, the composition described herein is stored in a glass bottle with or without a liquid dispenser. In certain embodiments, the plastic or glass bottle is opaque.

Additionally, the compositions described herein are either packaged for single use or for multiple uses with or without a preservative.

Certain Pharmaceutical and Medical Terminology

The term "acceptable" with respect to a formulation, composition or ingredient, as used herein, means having no persistent detrimental effect on the general health of the subject being treated.

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

All of the various embodiments or options described herein can be combined in any and all variations. The following Examples serve only to illustrate the invention and are not to be construed in anyway to limit the invention.

EXAMPLES

Example 1

Exemplary Phenylephrine HCl Ophthalmic Formulation

R-Phenylephrine Hydrochloride Ophthalmic Solution, USP 2.5% or 10%, is a sterile, clear, colorless to light yellow, topical mydriatic agent for ophthalmic use. The chemical name is (R)-3-hydroxy-α-[(methylamino)methyl]benzenemethanol hydrochloride. R-Phenylephrine hydrochloride is represented by the following structural formula:

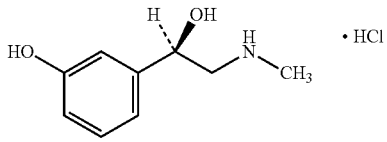

Phenylephrine hydrochloride has a molecular weight of 203.67 and an empirical formula of $C_9H_{13}NO_2$·HCl.

Each mL of R-Phenylephrine Hydrochloride Ophthalmic Solution, 2.5% contains: ACTIVE: phenylephrine hydrochloride 25 mg (2.5%); INACTIVES: sodium phosphate monobasic, sodium phosphate dibasic; boric acid, water for injection. Hydrochloric acid and/or sodium hydroxide may be added to adjust pH (6.0 to 6.4). The solution has a tonicity of 500 mOsm/kg; PRESERVATIVE: benzalkonium chloride 0.01%.

Each mL of R-Phenylephrine Hydrochloride Ophthalmic Solution, 10% contains: ACTIVE: R-phenylephrine hydrochloride 100 mg (10%); INACTIVES: sodium phosphate monobasic, sodium phosphate dibasic; water for injection. Hydrochloric acid and/or sodium hydroxide may be added to adjust pH (6.3 to 6.7). The solution has a tonicity of 1000 mOsm/kg; PRESERVATIVE: benzalkonium chloride 0.01%.

The composition of Phenylephrine HCl Ophthalmic Solution, 2.5% and 10% is listed in Table 1.

Table 1: Phenylephrine HCl Ophthalmic Solution, 2.5% and 10% Quantitative Composition

| Component | 2.5% Formulation Quantity (% w/v) | 10% Formulation Quantity (% w/v) | Function | Quality Standard |
| --- | --- | --- | --- | --- |
| R-Phenylephrine HCl | 2.5% | 10% | Active | USP |
| Sodium Phosphate Monobasic, | 0.5% | 0.5% | Buffer | USP |
| Sodium Phosphate Dibasic, Anhydrous | 0.3% | 0.3% | Buffer | USP |
| Boric Acid | 1.0% | | Buffer | USP |
| Benzalkonium Chloride | 0.01% | 0.01% | Antimicrobial preservative | USP |
| Sodium Hydroxide | As needed | As needed | pH adjustment | USP |
| Hydrochloric Acid | As needed | As needed | pH adjustment | USP |

Example 2

Stability (Impurity) Test and Results

Stability studies of 2.5% and 10% Phenylephrine HCL solutions prepared as in Example 2 were conducted at 2 to 8° C. for 12 months.

While the testing performed during the historical stability analysis is limited, those parameters evaluated show excellent results. For the 3 batches of 2.5% formulation evaluated, the initial assay averaged 101.2% of label claim (range 99.8%-102.9%), and after 12 months of storage at the labeled storage condition (2-8° C.) the average potency was 99.7% of label claim (range 97.0%-103.4%). All other parameters evaluated (appearance, preservative effectiveness, sterility) conformed to specifications.

For the 3 batches of 10% formulation evaluated, the initial assay averaged 100.4% of label claim (range 99.8%-101.6%), and after 12 months of storage at the labeled storage condition (2-8° C.) the average potency was 99.8% of label claim (range 98.8%-101.0%). All other parameters evaluated (appearance, preservative effectiveness, sterility) conformed to specifications.

Example 3

Chiral HPLC Analysis

The following are non-limited exemplary chiral columns and relevant mobile phases in the methods for analyzing chiral purity of R-phenylephrine.

Column-OJ-RH (150×4.6) mm, 5 µm, Flow: 1 mL min-1, Mobile Phase: Methanol, Column Temp: 25° C., Detection wavelength: 270 nm.

Column-OJ-RH (150×4.6) mm, 5 µm, Flow: 0.8 mL min-1, Mobile Phase: 0.05% Ethylenediamine in Methanol, Column Temp: 25° C., Detection wavelength: 270 nm.

Column-OJ-RH (150×4.6) mm, Flow: 1 ml min-1, Mobile Phase: 0.05% Ethylenediamine in Methanol, Column Temp: Ambient, Detection wavelength: 270 nm.

Column-OJ-RH (150×4.6) mm, 5 μm, Flow: 1 ml min-1, Mobile Phase: 0.05% Ethylenediamine in Methanol, Column Temp: 25° C., Detection wavelength: 270 nm.

Column-OJ-RH (150×4.6) mm, 5 μm, Flow: 1 ml min-1, Mobile Phase: 0.05 Ethylenediamine in Methanol, Column Temp: 25° C., Detection wavelength: 270 nm.

Column-OJ-RH (150×4.6) mm, 5 μm, Flow: 1 ml min-1, Mobile Phase: 0.05% Ethylenediamine in Water (05%): Methanol (95), Column Temp: 25° C., Detection wavelength: 270 nm.

Column-OJ-RH (150×4.6) mm, 5 μm, Flow: 1 ml min-1, Mobile Phase: 0.05% Ethylenediamine in Methanol, Column Temp: 25° C., Detection wavelength: 270 nm.

Column-OJ-RH (150×4.6) mm, 5 μm, Flow: 1 ml min-1, Mobile Phase: 0.05% Ethylenediamine in Methanol, Column Temp: 25° C., Detection wavelength: 270 nm.

Column-OJ-RH (150×4.6) mm, 5 μm, Flow: 0.5 ml min-1, Mobile Phase: Acetonitrile: 0.05% Ethylenediamine in water (30:70) Column Temp.: 25° C., Detection wavelength: 270 nm.

Column-OJ-RH (150×4.6) mm, 5 μm, Flow: 0.5 ml min-1; Mobile Phase: Acetonitrile: 0.05% Ethylenediamine in water (40:60) Column Temp.: 25, Detection wavelength: 270 nm.

Column-Chiralpak IC-3 (150×4.6) mm, 3 μm, Flow: 1.0 ml min-1, Mobile Phase: 0.1% Ethylenediamine in n-Hexane (85%): Ethanol (15%), Column Temp: 25° C., Detection wavelength: 270 nm; ref 600 nm.

Column-Chiralpak IC-3 (150×4.6) mm, 3 μm, Flow: 1.2 ml min-1, Mobile Phase: 0.1% Ethylenediamine in n-Hexane (50%): IPA (50%), Column Temp: 25° C., Detection wavelength: 270 nm.

Column-OJ-RH (150×4.6) mm, Flow: 0.6 ml min-1, Mobile Phase: 0.05% Ethylenediamine in Methanol, Column Temp: 25° C.; Detection wavelength: 270 nm. 4.0 mg sample in 1 mL ethanol was analyzed. The injection volume to HPLC is 3.0 μL. The HPLC chromatogram is shown in FIG. 1.

The HPLC chromatogram clearly show separation of racemic sample. Chiral HPLC method was thus established to analyze Phenylephrine.

Example 4

Determination of Chiral Purity after 6 Months Storage at Low Temperature

Figure 2:
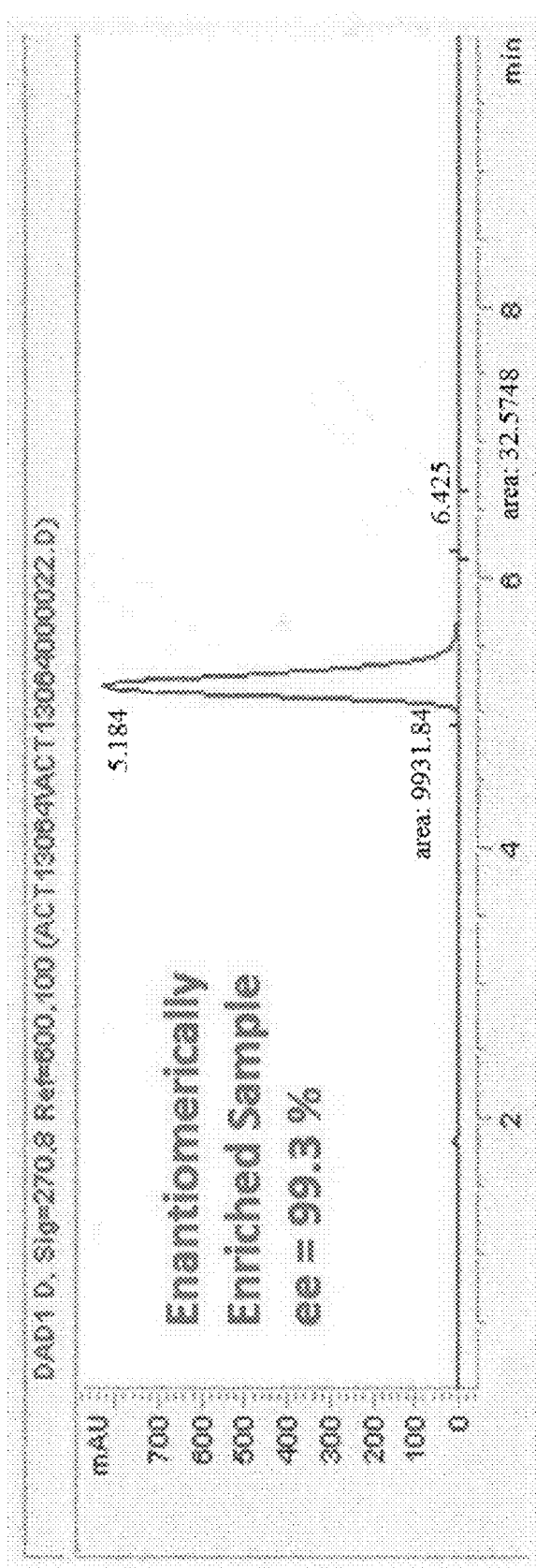
FIG. 2 shows a HPLC chromatogram of the exemplary R-Phenylephrine Hydrochloride Opthalmic Solution (10%) before storage. The chiral purity was determined to be 99.3% ee based on the peaks at 5.184 minutes (area: 9931.84) and at 6.425 minutes (area: 32.5748).

R-Phenylephrine Hydrochloride Opthalmic Solution, 2.5% and 10% prepared as in Example 1 were stored at 2 to 8° C. The chiral purity of Sample 1 (10% solution) was assessed before low temperature stability test. The HPLC chromatogram is shown in FIG. 2.

The chiral purity of R-Phenylephrine Hydrochloride was determined by the method and conditions as shown in Example 3. The result showed 99.3% ee.

Figure 3:
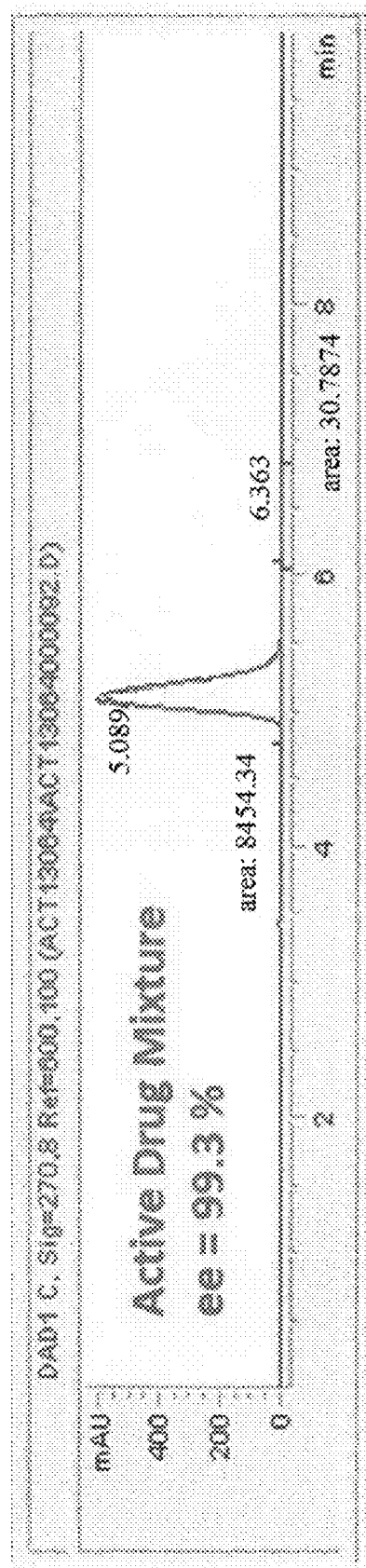
FIG. 3 shows a HPLC chromatogram of the exemplary R-Phenylephrine Hydrochloride Opthalmic Solution (10%) stored at 2 to 8° C. after 6 months. The chiral purity was determined to be 99.3% ee based on the peaks at 5.089 minutes (area: 8454.34) and at 6.363 minutes (area: 30.7874).

After 6 months of low temperature storage (i.e., 2 to 8° C.), the chiral purity of R-Phenylephrine Hydrochloride in the solution was determined to be 99.3% ee. The HPLC chromatogram is shown in FIG. 3.

Figure 4:
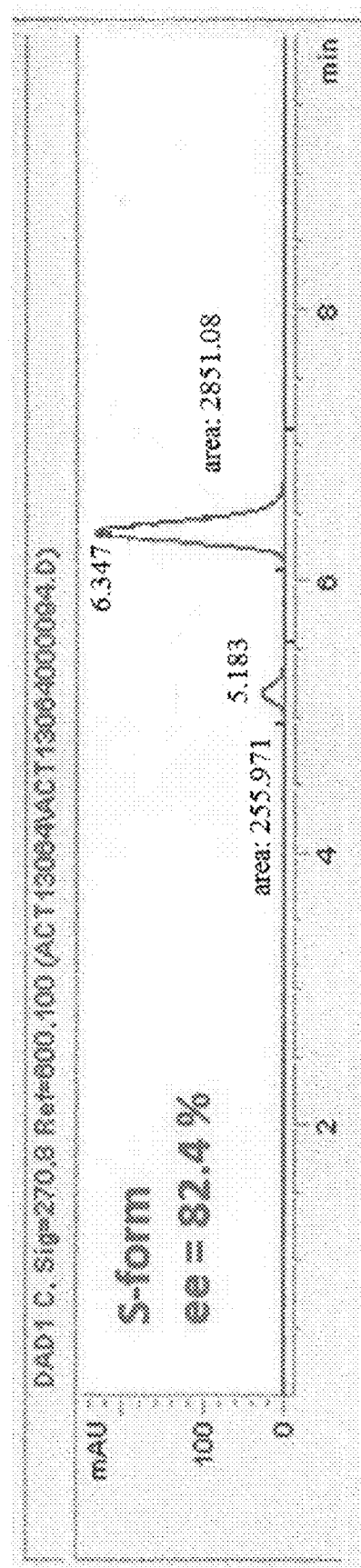
FIG. 4 shows a HPLC chromatogram of the purified "impurity" which is a S-Phenylephrine Hydrochloride. The chiral purity was determined to be 82.4% ee based on the peaks at 5.183 minutes (area: 255.971) and at 6.347 minutes (area: 2851.08).

To confirm the "impurity" shown in the chromatogram, the "impurity" was purified and determined by the same method. The "impurity" (i.e., S-Phenylephrine Hydrochloride) was determined to possess 82.4% ee of S-form. The HPLC chromatogram is shown in FIG. 4.

Thus, it is clearly shown that the solution remain substantially maintains the initial chiral purity of R-phenylephrine hydrochloride for at least 6 months.

Example 5

Dilation Assay of S Form Phenylephrine Solution

Both R and S form solutions (10% solution prepared as in Example 1) were test for dilation on rabbits. The first test rabbit received 3 drops of the S form formulation and the second test rabbit received 3 drops of the R form solution.

The results were as follows:

Test Rabbit No. 1: Minimal Dilation, within 15 minutes of dilation the pupil was only slightly more dilated than the untreated eye. The treated eye responded to light exposure and constricted slowly. The control eye constricted rapidly as was expected.

Test Rabbit No 2: Maximal dilation within 15 minutes of dosing. The pupil did not respond to light exposure and remained fully dilated for 4 hours then regressed.

These results clearly show that an ophthalmic solution of phenylephrine containing S-isomer does not dilate the rabbit pupil as it is achieved with an ophthalmic solution of phenylephrine containing R isomer. Thus it is evident that maintaining the chiral purity of the ophthalmic solution is crucial to keep drug potency.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of using an ophthalmic composition for pupil dilation, the composition comprising R-phenylephrine hydrochloride having an initial chiral purity of at least 95% and an aqueous buffer, wherein the chiral purity of R-phenylephrine hydrochloride is at least 95% of the initial chiral purity after 6 months, the method comprising:
   administering the composition into an eye of an individual in need thereof, wherein the composition is stored between −10 to 10 degree Celsius prior to administration, and wherein the composition comprises R-phenylephrine hydrochloride having a chiral purity of at least 95% when administered after storage.

2. The method of claim 1, wherein the composition is allowed to be stored between 2 to 8 degree Celsius.

3. The method of claim 1, wherein the composition comprises R-phenylephrine hydrochloride having an initial chiral purity of at least 99%.

4. The method of claim 1, wherein the composition comprises R-phenylephrine hydrochloride having an initial chiral purity of at least 99.3%.

5. The method of claim 1, wherein the chiral purity of R-phenylephrine hydrochloride is at least 97% of the initial chiral purity after 6 months.

6. The method of claim 1, wherein the chiral purity of R-phenylephrine hydrochloride is at least 99% of the initial chiral purity after 6 months.

7. The method of claim 1, wherein the chiral purity of R-phenylephrine hydrochloride is at least 99.5% of the initial chiral purity after 6 months.

8. The method of claim 1, wherein the composition comprises 2.5% w/v or 10% w/v R-phenylephrine hydrochloride by weight.

9. The method of claim 1, wherein the composition is packaged in a 1-15 ml plastic or glass bottle.

10. The method of claim 9, wherein the package identifies storing the composition at a temperature between −10 to 10 C.

11. The method of claim 10, wherein the package identifies storing the composition at a temperature between 2 to 8 C.

12. The method of claim 9, wherein the composition is in a plastic or glass bottle of about 2 ml, about 3 ml, about 5 ml, about 10 ml or about 15 ml.

13. The method of claim 9, wherein the plastic or glass bottle is opaque.

* * * * *